US012071635B2

(12) United States Patent
Cavazzana et al.

(10) Patent No.: US 12,071,635 B2
(45) Date of Patent: *Aug. 27, 2024

(54) METHOD FOR GENERATING T-CELL PROGENITORS

(71) Applicants: Assistance Publique-Hopitaux de Paris, Paris (FR); Fondation Imagine-Institut Des Maladies Genetiques, Paris (FR); Universtie Paris Descartes, Paris (FR); Institut National de la Sante et de la Recherche Medicale (INSERM), Paris (FR)

(72) Inventors: Marina Cavazzana, Paris (FR); Isabelle André, Meudon (FR); Chantal Lagresle-Peyrou, Montrouge (FR); Salima Hacein-Bey-Abina, La Garenne Colombes (FR); Christian Reimann, Freiburg (DE); Corinne De Chappedelaine, Paris (FR); Emmanuelle Six, Saint Geneviève des Bois (FR)

(73) Assignees: ASSISTANCE PUBLIQUE-HOPITAUX DE PARIS, Paris (FR); FONDATION IMAGINE-INSTITUT DES MALADIES GÉNÉTIQUES, Paris (FR); UNIVERSITÉCITÉ, Paris (FR); INSTITUT NATIONAL DE LA SANTÉET DE LA RECHERCHE MÉDICALE (INSERM), Paris (FR)

( * ) Notice: Subject to any disclaimer, the term of this patent is extended or adjusted under 35 U.S.C. 154(b) by 70 days.

This patent is subject to a terminal disclaimer.

(21) Appl. No.: 15/516,731

(22) PCT Filed: Oct. 5, 2015

(86) PCT No.: PCT/EP2015/072889
§ 371 (c)(1),
(2) Date: Apr. 4, 2017

(87) PCT Pub. No.: WO2016/055396
PCT Pub. Date: Apr. 14, 2016

(65) Prior Publication Data
US 2018/0208895 A1 Jul. 26, 2018

(30) Foreign Application Priority Data
Oct. 6, 2014 (FR) ..................................... 1459539

(51) Int. Cl.
*C12N 5/00* (2006.01)
*C12N 5/0783* (2010.01)

(52) U.S. Cl.
CPC ........ *C12N 5/0636* (2013.01); *C12N 2501/42* (2013.01); *C12N 2502/1114* (2013.01); *C12N 2506/11* (2013.01); *C12N 2533/50* (2013.01); *C12N 2533/52* (2013.01)

(58) Field of Classification Search
USPC ........................................................ 435/325
See application file for complete search history.

(56) References Cited

U.S. PATENT DOCUMENTS

| 6,093,531 A | 7/2000 | Bjornson et al. |
| 10,543,257 B2 * | 1/2020 | Uchida ................ C07K 14/805 |
| 2011/0052554 A1 | 3/2011 | Zakrzewski et al. |
| 2013/0095079 A1 | 4/2013 | Bernstein et al. |
| 2014/0349402 A1 | 11/2014 | Cooper et al. |
| 2014/0369973 A1 | 12/2014 | Bernstein et al. |
| 2017/0128556 A1 | 5/2017 | Kawamoto et al. |
| 2017/0158749 A1 | 6/2017 | Cooper et al. |

FOREIGN PATENT DOCUMENTS

| JP | 2012508188 A | 4/2012 |
| JP | 2016526913 A | 9/2016 |
| RU | 2535966 C2 | 12/2014 |
| WO | 1999028486 A1 | 6/1999 |
| WO | 2010031006 A1 | 3/2010 |
| WO | 2010051634 A1 | 5/2010 |
| WO | WO 2011/068962 | 6/2011 |
| WO | WO 2014/110353 | 7/2014 |
| WO | 2015017755 A1 | 2/2015 |
| WO | 2015099134 A1 | 2/2015 |
| WO | 2015162211 A1 | 10/2015 |

OTHER PUBLICATIONS

Lamer et al (Cytotherapy 2008, vol. 10, No. 4, pp. 406-416).*
Reimann et al. (Blood vol. 114, No. 22, p. 3532, 2009).*
Takara Product Manual for RetroNectin® (2017).*
Milliano (J. Hepataology, 2003, p. 32-37).*
Yanase (Biochem. & Biophys. Res. Comm., 2000, vol. 277, p. 72-78).*
Wijelath, "Fibronectin promotes VEGF-induced CD34 cell differentiation into endothelial cells", J Vasc Surg, 2004, 39:655-660.*
Awong et al., *Characterization in vitro and engraftment potential in vivo of human progenitor T cells generated from hematopoietic stem cells,* 114(5) Blood 972-982 (2009).
Cardin et al. *Molecular modeling of protein-glycosaminoglycan interactions,* 9 Arteriosclerosis, Thrombosis, and Vascular Biology 21-32 (1989) (abstract only).

(Continued)

Primary Examiner — Michael C Wilson
(74) Attorney, Agent, or Firm — Panitch Schwarze Belisario & Nadel LLP; Erin M. Dunston

(57) ABSTRACT

The invention relates to the field of cell therapy and to an in vitro method for generating T-cell progenitors, comprising the step of exposing CD34+ cells in a medium containing a Notch ligand, a soluble domain of the Delta-like ligand 4, joined to an Fc region of a protein IgG, in the presence of a fragment of fibronectin comprising the motifs RGDS and CS-1 and a heparin-binding domain.

16 Claims, 3 Drawing Sheets

Specification includes a Sequence Listing.

(56) References Cited

OTHER PUBLICATIONS

Chono et al., *Removal of inhibitory substances with recombinant fibronectin-CH-296 plates enhances the retroviral transduction efficiency of CD34(+)CD38(−) bone marrow cells,* 130(3) Journal of Biochemistry 331-334 (Sep. 2001).
Delaney et al., *Notch-mediated expansion of human cord blood progenitor cells capable of rapid myeloid reconstitution,* 16(2) Nature Medicine 232-236 (Feb. 2010).
Jonuleit et al., *Pro-inflammatory cytokines and prostaglandins induce maturation of potent immunostimulatory dendritic cells under fetal calf serum-free conditions,* 27(12) European Journal of Immunology 3135-3142 (Dec. 1997).
Kimizuka et al., *Production and characterization of functional domains of human fibronectin expressed in Escherichia coli,* 110(2) Journal of Biochemistry 284-291 (Aug. 1991).
Luft et al., *Type I IFNs enhance the terminal differentiation of dendritic cells,* 161(4) Journal of Immunology 1947-1953 (Aug. 15, 1998).
Meek et al., *In vitro-differentiated T/natural killer-cell progenitors derived from human CD34+ cells mature in the thymus,* 115(2) Blood 261-264 (Jan. 14, 2010).
Ohishi et al., *Delta-1 enhances marrow and thymus repopulating ability of human CD34(+)CD38(−) cord blood cells,* 110(8) Journal of Clinical Investigation 1165-1174 (Oct. 2002).
Wayner et al., *Identification and characterization of the T lymphocyte adhesion receptor for an alternative cell attachment domain (CS-1) in plasma fibronectin,* 109(3) Journal of Cell Biology 1321-1330 (Sep. 1989).
Weinmaster, *Notch signal transduction: a real rip and more,* 10(4) Current Opinion in Genetics & Development 363-369 (Aug. 2000).
Zakrzewski et al., *Adoptive transfer of T-cell progenitors enhances T-cell reconstitution after allogeneic hematopoietic stem cell transplantation,* 12(9) Nature Medicine 1039-1047 (Sep. 2006).
Frassoni et al., *Cord blood transplantation provides better reconstitution of hematopoietic reservoir compared with bone marrow transplantation,* 102(3) Blood 1138-1141 (Aug. 1, 2003).
Kim et al., *Ligand-Functionalized Biomaterial Surfaces: Controlled Regulation of Signaling Pathways to Direct Stem Cell Differentiation,* Biological Interactions on Materials Surfaces 157-171 (2009).
Lansdorp et al., *Ontogeny-related Changes in Proliferative Potential of Human Hematopoietic Cells,* 178 J. Exp. Med. 787-791 (Sep. 1993).
Lefort et al., *Short exposure to Notch ligand Delta-4 is sufficient to induce T-cell differentiation program and to increase the T cell potential of primary human CD34$^+$ cells,* 34 Experimental Hematology 1720-1729 (2006).
Liang et al., *Effects of again on the homing and engraftment of murine hematopoietic stem and progenitor cells,* 106 Blood 1479-1487 (2005).
RetroNectin Cat.# T100A/B, v. 0603 Takara-Bio (undated, before Apr. 4, 2017).
Reimann et al., *Human T-lymphoid Progenitors Generated in a Feeder-Cell-Free Delta-Like-4 Culture System Promote T-Cell Reconstitution in NOD/SCID/γc$^{−/−}$ Mice,* 30 Stem Cells 1771-1780 (2012).
Rosler et al., *An in vivo competitive repopulation assay for various sources of human hematopoietic stem cells,* 96 Blood 3414-3421 (2000).
Six et al., *A human postnatal lymphoid progenitor capable of circulating and seeding the thymus,* 204(13) JEM 3085-3093 (Dec. 24, 2007).
Six et al., *Cytokines and culture medium have a major impact on impact on human in vitro T-cell differentiation,* 47 Blood Cells, Molecules, and Diseases 72-78 (2011).
Szilvassy et al., *Differential homing and engraftment properties of hematopoietic progenitor cells form murine bone marrow, mobilized peripheral blood, and fetal liver,* 98 Blood 2108-2115 (2001).

Varnum-Finney et al., *Immobilization of Notch ligand, Delta-1, is required for induction of Notch signaling,* 113 Journal of Cell Science 4313-4318 (2000).
Yuan et al., *Lin28b reprograms adult bone marrow hematopoietic progenitors to mediate fetal-like lymphopoiesis,* 335(6073) Science 1195-1200 (Mar. 9, 2012).
Huijskens et al., *Technical Advance: Ascorbic acid induces development of double-positive T cells from human hematopoietic stem cells in the absence of stromal cells,* 96(6) Journal of Leukocyte Biology 1165-1175 (Dec. 2014).
Product information for DLL4 protein from Sino Biological (not later than Dec. 31, 2014).
Cavazzana-Calvo et al. "Human hematopoiesis: from CD34 cells to T lymphocytes" (in English), Medecine/Sciences, 2006; 22: 151-9.
Ohishi et al. "The Notch ligand, Delta-1, inhibits the differentiation of monocytes into macrophages but permits their differentiation into dendritic cells", Blood, Sep. 1, 2001;98(5):1402-7.
Dik et al. "New insights on human T cell development by quantitative T cell receptor gene rearrangement studies and gene expression profiling", J Exp Med., Jun. 6, 2005;201(11):1715-23.
Boitano et al. "Aryl hydrocarbon receptor antagonists promote the expansion of human hematopoietic stem cells", Science, Sep. 10, 2010;329(5997):1345-8.
http://catalog.takara-bio.co.jp/product/basic_info.php?unitid=U100002954 (Aug. 1, 2010).
Awong et al. "Human proT-cells generated in vitro facilitate hematopoietic stem cell-derived T-lymphopoiesis in vivo and restore thymic architecture", Blood, Dec. 19, 2013;122(26):4210-9.
Gori et al. "Efficient generation, purification, and expansion of CD34(+) hematopoietic progenitor cells from nonhuman primate-induced pluripotent stem cells", Blood, Sep. 27, 2012;120(13):e35-44.
Thordardottir et al. "The aryl hydrocarbon receptor antagonist StemRegenin 1 promotes human plasmacytoid and myeloid dendritic cell development from CD34+ hematopoietic progenitor cells", Stem Cells Dev., May 1, 2014;23 (9).955-67.
Feng et al. "Expansion of engrafting human hematopoietic stem/progenitor cells in three-dimensional scaffolds with surface-immobilized fibronectin", J Biomed Mater Res A., Sep. 15, 2006; 78(4): 781-791.
Snoeck Hans-W et al., "Tumor necrosis factor alpha is a potent synergistic factor for the proliferation of primitive human hematopoietic progenitor cells and induces resistance to transforming growth factor beta but not to interferon gamma", The Journal of Experimental Medicine, Feb. 1, 1996, vol. 183, No. 2, pp. 705-710 (6 pp.).
Weekx Steven F A et al., "Generation of T cells from adult human hematopoietic stem cells and progenitors in a fetal thymic organ culture system: stimulation by tumor necrosis factor-alpha", Blood, May 1, 2000, vol. 95, No. 9, pp. 2806-2812 (7 pp.).
Jaleco A.C. et al., "Differential effects of Notch ligands Delta-1 and Jagged-1 in human lymphoid differentiation" J Exp Med. Oct. 1, 2001;194(7):991-1002. doi: 10.1084/jem.194.7.991.
Hacein-Bey et al., "Optimization of retroviral gene transfer protocol to maintain the lymphoid potential of progenitor cells" Hum Gene Ther. Feb. 10, 2001;12(3):291-301.
Smits et al. "Tumor necrosis factor promotes T-cell at the expense of B-cell lymphoid development from cultured human CD34φ cord blood cells" Experimental Hematology 35. 2007, 1272-1278.
Besseyrias et al. "Hierarchy of Notch-Delta interactions promoting T cell lineage commitment and maturation" J. Exp. Med. 2007, 204(2):331-43.
Dahlberg et al. "Ex vivo expansion of human hematopoietic stem and progenitor cells" Blood. 2011, 117(23):6083-90.
Delaney et al. "Notch-mediated Expansion of Human Cord Blood Progenitor Cells Capable of Rapid Myeloid Reconstitution" Nat Med. 2010, 16(2): 232.
Hozumi et al. "Delta-like 4 is indispensable in thymic environment specific for T cell development" J. Exp. Med. 2008, vol. 205 No. 11 2507-2513.
Koch et al. "Delta-like 4 is the essential, nonredundant ligand for Notch1 during thymic T cell lineage commitment" J. Exp. Med. 2008, vol. 205 No. 11 2515-2523.

(56) References Cited

OTHER PUBLICATIONS

Ross A. Kopher et al., Human embryonic stem cell-derived CD34+ cells function as MSC progenitor cells, Bone, 2010, 47(4), pp. 718-728, doi:10.1016/j.bone.2010.06.020.
Reimann et al, "Further Characterization of T-Cellular Precursors Generated From CD34+ Progenitors by Exposure to Immobilized Notch Ligand Delta-Like 4 In Vitro." Blood, American society of Hematology, Nov. 2010,p. 3712.
McBeath et al., Cell Shape, Cytoskeletal Tension, and RhoA, Regulate Stem Cell Lineage Commitment, 6 Developmental Cell 483-495, Apr. 2004.
Singh et al., Fibronectin and stem cell differentiation—lessons from chondrogenesis, 125(16) Journal of Cell Science 3703-3712 (2012).
Van Lent et al., Functional Human Antigen Specific T Cells Produced In Vitro Using Retroviral T Cell Receptor Transfer Into Hematopoietic Progenitors, 179 The Journal of Immunology 4959-4968 (2007).

* cited by examiner

A.

B.

SEQUENCE LISTING

<160> NUMBER OF SEQ ID NOS: 7

<210> SEQ ID NO 1
<211> LENGTH: 723
<212> TYPE: PRT
<213> ORGANISM: artificial
<220> FEATURE:
<223> OTHER INFORMATION: human Delta-1 (soluble fraction 1-536) G502 may be R

<400> SEQUENCE: 1

```
Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
            340                 345                 350
```

```
Thr Cys Pro Pro Gly Phe Tyr Lys Ile Cys Glu Leu Ser Ala Met
            355                 360                 365
Thr Cys Ala Asp Gly Pro Cys Phe Asn Gly Gly Arg Cys Ser Asp Ser
370                 375                 380
Pro Asp Gly Gly Tyr Ser Cys Arg Cys Pro Val Gly Tyr Ser Gly Phe
385                 390                 395                 400
Asn Cys Glu Lys Lys Ile Asp Tyr Cys Ser Ser Pro Cys Ser Asn
            405                 410                 415
Gly Ala Lys Cys Val Asp Leu Gly Asp Ala Tyr Leu Cys Arg Cys Gln
            420                 425                 430
Ala Gly Phe Ser Gly Arg His Cys Asp Asn Val Asp Asp Cys Ala
            435                 440                 445
Ser Ser Pro Cys Ala Asn Gly Gly Thr Cys Arg Asp Gly Val Asn Asp
450                 455                 460
Phe Ser Cys Thr Cys Pro Pro Gly Tyr Thr Gly Arg Asn Cys Ser Ala
465                 470                 475                 480
Pro Val Ser Arg Cys Glu His Ala Pro Cys His Asn Gly Ala Thr Cys
            485                 490                 495
His Glu Arg Gly His Gly Tyr Val Cys Glu Cys Ala Arg Gly Tyr Gly
            500                 505                 510
Gly Pro Asn Cys Gln Phe Leu Leu Pro Glu Leu Pro Pro Gly Pro Ala
            515                 520                 525
Val Val Asp Leu Thr Glu Lys Leu Glu Gly Gln Gly Gly Pro Phe Pro
            530                 535                 540
Trp Val Ala Val Cys Ala Gly Val Ile Leu Val Leu Met Leu Leu Leu
545                 550                 555                 560
Gly Cys Ala Ala Val Val Val Cys Val Arg Leu Arg Leu Gln Lys His
            565                 570                 575
Arg Pro Pro Ala Asp Pro Cys Arg Gly Glu Thr Glu Thr Met Asn Asn
            580                 585                 590
Leu Ala Asn Cys Gln Arg Glu Lys Asp Ile Ser Val Ser Ile Ile Gly
            595                 600                 605
Ala Thr Gln Ile Lys Asn Thr Asn Lys Lys Ala Asp Phe His Gly Asp
610                 615                 620
His Ser Ala Asp Lys Asn Gly Phe Lys Ala Arg Tyr Pro Ala Val Asp
625                 630                 635                 640
Tyr Asn Leu Val Gln Asp Leu Lys Gly Asp Asp Thr Ala Val Arg Asp
            645                 650                 655
Ala His Ser Lys Arg Asp Thr Lys Cys Gln Pro Gln Gly Ser Ser Gly
            660                 665                 670
Glu Glu Lys Gly Thr Pro Thr Thr Leu Arg Gly Gly Glu Ala Ser Glu
            675                 680                 685
Arg Lys Arg Pro Asp Ser Gly Cys Ser Thr Ser Lys Asp Thr Lys Tyr
690                 695                 700
Gln Ser Val Tyr Val Ile Ser Glu Glu Lys Asp Glu Cys Val Ile Ala
705                 710                 715                 720
Thr Glu Val

<210> SEQ ID NO 2
<211> LENGTH: 724
<212> TYPE: PRT
<213> ORGANISM: artificial
<220> FEATURE:
<223> OTHER INFORMATION: human Delta-4 protein (soluble fraction 1-526)
```

<400> SEQUENCE: 2

```
Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415
```

```
Cys Leu Asn Arg Gly Pro Ser Arg Met Cys Arg Cys Arg Pro Gly Phe
                420                 425                 430

Thr Gly Thr Tyr Cys Glu Leu His Val Ser Asp Cys Ala Arg Asn Pro
            435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
        610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val Thr Pro Arg
        675                 680                 685

Leu Asp Leu Pro Ser Ala Leu Phe Thr Leu His Pro Gly Trp Asp Val
        690                 695                 700

Phe His Met Gln Arg Ala Ala Leu Arg Arg Arg Glu Trp Gln Glu
705                 710                 715                 720

Pro Asp Arg Leu

<210> SEQ ID NO 3
<211> LENGTH: 4
<212> TYPE: PRT
<213> ORGANISM: artificial
<220> FEATURE:
<223> OTHER INFORMATION: Motif RGDS

<400> SEQUENCE: 3

Arg Gly Asp Ser
1

<210> SEQ ID NO 4
<211> LENGTH: 6
<212> TYPE: PRT
<213> ORGANISM: artificial
<220> FEATURE:
```

```
<223> OTHER INFORMATION: heparin binding domain XBBXBX; B = basic amino
      acid; X = hydropathic amino acid
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 4

Xaa Asx Asx Xaa Asx Xaa
1               5

<210> SEQ ID NO 5
<211> LENGTH: 8
<212> TYPE: PRT
<213> ORGANISM: artificial
<220> FEATURE:
<223> OTHER INFORMATION: heparin binding domain XBBBXXBX;
      B = basic amino acid; X = hydropathic amino acid
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 5

Xaa Asx Asx Asx Xaa Xaa Asx Xaa
1               5

<210> SEQ ID NO 6
<211> LENGTH: 25
<212> TYPE: PRT
<213> ORGANISM: artificial
<220> FEATURE:
<223> OTHER INFORMATION: Motif CS-1

<400> SEQUENCE: 6

Asp Glu Leu Pro Gln Leu Val Thr Leu Pro His Pro Asn Leu His Gly
1               5                   10                  15

Pro Glu Ile Leu Asp Val Pro Ser Thr
            20                  25

<210> SEQ ID NO 7
<211> LENGTH: 754
<212> TYPE: PRT
<213> ORGANISM: artificial
<220> FEATURE:
<223> OTHER INFORMATION: fusion protein human delta 4 - Fc receptor

<400> SEQUENCE: 7

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
```

```
                35                  40                  45
Pro Cys Glu Pro Gly Cys Arg Thr Phe Phe Arg Val Cys Leu Lys His
 50                  55                  60

Phe Gln Ala Val Val Ser Pro Gly Pro Cys Thr Phe Gly Thr Val Ser
 65                  70                  75                  80

Thr Pro Val Leu Gly Thr Asn Ser Phe Ala Val Arg Asp Asp Ser Ser
                 85                  90                  95

Gly Gly Gly Arg Asn Pro Leu Gln Leu Pro Phe Asn Phe Thr Trp Pro
                100                 105                 110

Gly Thr Phe Ser Leu Ile Ile Glu Ala Trp His Ala Pro Gly Asp Asp
                115                 120                 125

Leu Arg Pro Glu Ala Leu Pro Pro Asp Ala Leu Ile Ser Lys Ile Ala
                130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
                180                 185                 190

Asp His Phe Gly His Tyr Val Cys Gln Pro Asp Gly Asn Leu Ser Cys
                195                 200                 205

Leu Pro Gly Trp Thr Gly Glu Tyr Cys Gln Gln Pro Ile Cys Leu Ser
210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
                260                 265                 270

Asp Glu Gly Trp Gly Gly Leu Phe Cys Asp Gln Asp Leu Asn Tyr Cys
                275                 280                 285

Thr His His Ser Pro Cys Lys Asn Gly Ala Thr Cys Ser Asn Ser Gly
                290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
                340                 345                 350

Gly Tyr Tyr Gly Leu His Cys Glu His Ser Thr Leu Ser Cys Ala Asp
                355                 360                 365

Ser Pro Cys Phe Asn Gly Gly Ser Cys Arg Glu Arg Asn Gln Gly Ala
                370                 375                 380

Asn Tyr Ala Cys Glu Cys Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
                420                 425                 430

Thr Gly Thr Tyr Cys Glu Leu His Val Ser Asp Cys Ala Arg Asn Pro
                435                 440                 445

Cys Ala His Gly Gly Thr Cys His Asp Leu Glu Asn Gly Leu Met Cys
450                 455                 460
```

```
Thr Cys Pro Ala Gly Phe Ser Gly Arg Arg Cys Glu Val Arg Thr Ser
465                 470                 475                 480
Ile Asp Ala Cys Ala Ser Ser Pro Cys Phe Asn Arg Ala Thr Cys Tyr
            485                 490                 495
Thr Asp Leu Ser Thr Asp Thr Phe Val Cys Asn Cys Pro Tyr Gly Phe
            500                 505                 510
Val Gly Ser Arg Cys Glu Phe Pro Val Gly Leu Pro Pro Ser Thr Met
            515                 520                 525
Val Arg Ser Val Glu Cys Pro Pro Cys Pro Ala Pro Pro Val Ala Gly
        530                 535                 540
Pro Ser Val Phe Leu Phe Pro Pro Lys Pro Lys Asp Thr Leu Met Ile
545                 550                 555                 560
Ser Arg Thr Pro Glu Val Thr Cys Val Val Val Asp Val Ser His Glu
                565                 570                 575
Asp Pro Glu Val Gln Phe Asn Trp Tyr Val Asp Gly Met Glu Val His
                580                 585                 590
Asn Ala Lys Thr Lys Pro Arg Glu Glu Gln Phe Asn Ser Thr Phe Arg
        595                 600                 605
Val Val Ser Val Leu Thr Val Val His Gln Asp Trp Leu Asn Gly Lys
        610                 615                 620
Glu Tyr Lys Cys Lys Val Ser Asn Lys Gly Leu Pro Ala Pro Ile Glu
625                 630                 635                 640
Lys Thr Ile Ser Lys Thr Lys Gly Gln Pro Arg Glu Pro Gln Val Tyr
                645                 650                 655
Thr Leu Pro Pro Ser Arg Glu Glu Met Thr Lys Asn Gln Val Ser Leu
                660                 665                 670
Thr Cys Leu Val Lys Gly Phe Tyr Pro Ser Asp Ile Ala Val Glu Trp
                675                 680                 685
Glu Ser Asn Gly Gln Pro Glu Asn Asn Tyr Lys Thr Thr Pro Pro Met
        690                 695                 700
Leu Asp Ser Asp Gly Ser Phe Phe Leu Tyr Ser Lys Leu Thr Val Asp
705                 710                 715                 720
Lys Ser Arg Trp Gln Gln Gly Asn Val Phe Ser Cys Ser Val Met His
                725                 730                 735
Glu Ala Leu His Asn His Tyr Thr Gln Lys Ser Leu Ser Leu Ser Pro
            740                 745                 750
Gly Lys
```

METHOD FOR GENERATING T-CELL PROGENITORS

CROSS-REFERENCE TO RELATED APPLICATIONS

This application is a U.S. National Stage Application pursuant to 35 U.S.C. § 371 of International Patent Application PCT/EP2015/072889, filed on Oct. 5, 2015, and published as WO 2016/055396 on Apr. 14, 2016, which claims priority to French Patent Application 1459539, filed on Oct. 6, 2014, all of which are incorporated herein by reference in their entireties for all purposes.

The invention relates to the field of cell therapy and in particular of transformed or non-transformed hematopoietic stem cell transplants, and to immune reconstitution following such transplants.

Transplantation of hematopoietic stem and progenitor cells (HSPCs) is considered to be the best therapeutic option for the most severe hereditary immune deficiencies, for numerous malignant hemopathies, and also for a certain number of solid tumors.

Currently, in allograft situations with partial HLA incompatibility, the injection, into preconditioned recipients, of increasing doses of sorted CD34+HSPCs allows the transplant from the donor to be engrafted with effective prevention of graft-versus-host disease (GVH). Nevertheless, the differentiation of new T lymophocytes from the injected CD34+ cells requires a minimum period of 4 months and these T lymphocytes are in a sufficient number to play a protective role against infections only a few months after they appear.

This slow immune reconstitution is responsible for the numerous infectious, in particular viral, complications, but also the relapses, which influence the long-term prognosis of transplanted patients.

Moreover, other therapeutic protocols use a gene therapy approach, that is to say an autograft of transduced HSPCs, which has demonstrated its efficacy in the treatment of certain hereditary immune deficits. The advantage of this strategy compared with allogenic CD34+HSPC transplantation is unquestionable in terms of survival and morbidity when no HLA-compatible donor is available. Nevertheless, clinical experience has shown that, for certain patients with severe infections, the reconstitution of the T lymphocyte compartment is slow and never reaches normal levels of circulating T lymphocytes. The morbidity and mortality associated with this particular context are high.

By virtue of the number of patients involved, and by virtue of the considerable morbidity and mortality which follows this type of transplantation, the development of new therapies aimed at decreasing the immunodeficiency period following the transplantation is fully justified.

It is thus important to accelerate the generation of T lymphocytes by administering precursors involved in the T lymphoid differentiation pathway (T-cell progenitors).

These T-cell precursors are derived from differentiation of CD34+HSPCS and exhibit in particular the CD7+ marker, which is a marker for differentiation in the T lymphocyte pathway. They can also exhibit other markers. Thus, Awong et al. (Blood 2009; 114:972-982) have described the following T lymphocyte precursors: early thymic progenitors (ETPs), which exhibit the (CD34+/CD45RA+/CD7+) markers, cells at the proT1 stage (CD7++/CD5−), cells at the proT2 stage (CD7++/CD5+), and cells at the preT stage (CD7++/CD5+CD1a+). The HSPCs thus acquire these markers successively while going through these steps, during T cell development.

A T precursor transplant concomitant with the HSPC transplant would make it possible to rapidly produce a mature and functional T lymphocyte compartment, and would as a result prevent the risk of severe infections, by enabling the patient to benefit from a minimum level of immunity before the total reconstitution of his immune system.

Moreover, it is important to be able to use adult cells rather than cord blood cells, since it is easier and less expensive to obtain adult cells than blood cord cells and they are more widely used in allograft.

However, the data published in the literature, obtained in human beings and mice, show intrinsic differences between fetal hematopoietic cells (including cord blood) and adult cells. These differences relate to the the capacity to repair DNA damage, the survival, proliferative capacity and the differentiation potential (see in particular Yuan et al. (Science. 2012 Mar. 9; 335 (6073): 1195-200), which indicate that the adult bone marrow cells are less efficient than fetal cells in terms of their potential for generating various cell types (Landsorp et al. (J Exp Med. 1993 Sep. 1; 178 (3): 787-91); Szilvassy et al. (Blood. 2001 Oct. 1; 98 (7): 2108-15); Frassoni et al. (Blood. 2003 Aug. 1; 102(3): 1138-41); Liang et al. (Blood. 2005 Aug. 15; 106(4): 1479-87); Six et al. (J Exp Med. 2007 Dec. 24; 204 (13): 3085-93)).

Notch proteins are transmembrane receptors which regulate the cell response to a large number of environmental signals. In mammals, 4 Notch receptors (Notch 1-4) and five ligands (Delta-like-1, 3, and 4, jagged1, jagged2) have been described (Weinmaster Curr Opin Genet Dev. 2000; 10:363-369).

The Notch ligands have several names. Thus, the Delta-like-ligand 4 ligand can be designated as:
Delta-like-ligand 4 (corresponding to the name of the DLL4 gene),
or by simplification Delta-like-4 or Delta ligand 4 (abbreviation DL-4).

In the present application, the Delta-like-1 and Delta-like-4 Notch ligands may be denoted respectively by DL1 and DL4 or DL-1 and DL-4. The sequences of the DL-1 and DL-4 ligands are specified as SEQ ID No. 1 and SEQ ID No. 2, respectively.

It has been shown that the interaction of Notch-1 with the DL-1 or DL-4 ligand plays an important role in early T lymphopoiesis.

Thus, several research groups have succeeded in inducing murine and human T differentiation in vitro by coculturing hematopoietic progenitors, for example with OP9 or Tst-4 stromal cells transduced with the DL-1 ligand or the DL-4 ligand. It has thus been shown that the precursors thus generated allow the production of mature T lymphocytes after transplantation into irradiated immunodeficient mice (see in particular Zakrzewski et al., Nat Med 2006 12(9): 1039 and Nat Biotech 2008 26(4): 453; Awong et al., Blood 2009 114 (5): 972; Meek et al., Blood 2010. 115:261-264).

However, the use of a genetically modified murin stroma cannot be envisaged in a clinical context.

It is a question of developing a process which makes it possible to generate and increase the number of CD7+T lymphocyte precursors from CD34+ hematopoietic stem cells without using cell stroma. Preferably, the hematopoietic stem cells have been isolated from an adult donor.

In the hope of replacing the OP9/DL1 stroma with a clinically more acceptable system, the inventors have tested various soluble Notch ligands, and demonstrated that a soluble form of the DL-4 ligand, fused with an Fc fragment of an immunoglobulin (DL4/Fc) makes it possible to generate CD7+ cells from cord blood CD34+ progenitors (Reimann et al., Stem Cells 2012; 30:1771-1780).

These studies have shown that 7 days of exposure to the DL4/Fc ligand make it possible to obtain a large number of CD7+CD34+/−T progenitors. Quantitative analysis by Taqman-PCR of the generated populations for the expression of the target genes of Notch and of the genes involved in T lymphocyte differentiation have shown that the phenotypic changes corresponded to a commitment into the T lymphoid differentiation pathway, in particular with an increase in pT$\alpha$, Rag1, 117R$\alpha$ and BCL11b, and decrease in a the expression of transcription factors involved in the myeloid and B lymphoid (in particular Pax5) differentiation pathways. Thus, the populations generated on DL4/Fc corresponded phenotypically and molecularly to the populations found in the human thymus.

These studies have also shown the absence of rearrangements of the T cell receptor loci. The T lymphoid potential of the progenitors generated in culture has been evaluated in vitro and in vivo. In vitro, the quantification of the T lymphoid potential under conditions of limiting dilutions in secondary cultures on an OP9 stroma expressing the DL-1 ligand has demonstrated a more than 200-fold increase compared with the non-cultured CD34+HSPCs. In vivo, this potential has been determined by injecting these cells into NOD/SCID/$\gamma$c−/− mice which have been irradiated for 4 weeks or which are newborn. Active thymopoiesis was found in 20/22 mice having received cells cultured on DL4/Fc, compared with 13/19 of the mice having received non-cultured CD34+ cells. Mature T lymphocytes were detected only in the recipients of cells cultured on DL4/Fc. The repertoire studies and the functional tests demonstrated that the T lymphocytes generated from the DL4/Fc T precursors exhibited a polyclonal repertoire and were functional.

These results show that exposure of the cord blood CD34+ cells to DL4/Fc allows the induction of T lymphoid development and the generation of a large number of T precursors in vitro. In addition, the precursors generated promote human thymopoiesis in vivo after transplantation of irradiated immunodeficient mice. Thus, although the prior publications made reference only to active thymopoiesis, mature human T cells circulate in the periphery in these mice very soon after the transplant.

However, this system has a certain number of limits: 1) From a quantitative point of view, the DL4/Fc system makes it possible to obtain approximately $6.5 \times 10^5$ T progenitors from $10^6$ cord blood CD34+ cells. This number could prove to be insufficient for an adult receiving a cord blood transplant.

2) The DL4/Fc molecule is immobilized on the plastic of culture dishes. This immobilization step is important for allowing the commitment of the HSPCs into the T lymphoid pathway. However, this system has three limits, in terms of:
immobilization efficiency,
half-life of the molecule immobilized,
binding of DL4/Fc to its Notch receptor at the surface of the CD34+HSPCs.

Delaney et al. (Nat Med. 2010 February; 16(2): 232) have described cultures of cord blood stem cells in the presence of a Notch ligand (DL-1). The objective was to accelerate hematopoietic reconstitution after transplantation. It should however be noted that the authors refer to increasing the number of "progenitors" and that this term in fact reflects the multipotent hematopoietic, in particular myeloid, progenitors and stem cells. The cells were cultured for 17-21 days.

Ohishi et al. (J Clin Invest. 2002 October; 110(8): 1165-74) cited in Delaney et al., also describe a culture of stem cells from cord blood in vitro for increasing the capacity for repopulation of the thymus and of the bone marrow during a transplant. The cells are also cultured for 17 or 18 days.

However, these authors do not describe the use of stem cells from adult donors, nor the culturing of these cells in order to use them to reconstitute a population of T lymphocyte precursors making it possible to provide a recipient with immune protection, in the weeks following a bone marrow transplant.

Kim and Roy (2009, in: "Biological interactions on materials surfaces", 2009, Puleo and Bizios, pages 157-171) disclose the use of biomaterials which have immobilized ligands in order to control and direct the differentiation of stem cells. The culturing of hematopoietic stem cells in the presence of microbeads exhibiting the Delta-like-4 Notch ligand assist their differentiation into T lymphocytes. Fibronectin immobilized on the cell support improves the stem cell expansion. Similar results are obtained with immobilized peptides comprising for example the RGDS and CS-1 motifs.

WO 2011/068962 describes processes for differentiating T or NK lymphocytes in vitro from hematopoietic stem cells or from precursor cells. The first step of the T lymphocyte differentiation enables process the production of T lymphocyte progenitors by culturing the stem cells on a layer of transformed OP-9 feeder cells expressing the DL1 Notch ligand. The first example illustrates the generation of T lymphocyte progenitors from murine bone marrow stem cells.

WO 2014/110353 relates to compositions comprising an osteoinductive Notch ligand bound to at least one biocompatible substrate. It also relates to processes for treating patients requiring bone tissue formation by administering a composition comprising an osteoinductive Notch ligand bound to at least one biocompatible substrate.

It is thus necessary to develop a novel method which makes it possible to improve the amount of T lymphocyte precursors generated from CD34+ cells. Moreover, this method should also make it possible to obtain T lymphocyte precursors, including from transduced CD34+HSPCs, which can be applicable to adult CD34+ cells for allogenic grafts or autografts, thus making it possible to overcome the relatively low number of cord blood cells.

The inventors have shown that it is possible to improve the amount of T cell precursors from CD34+ cells by exposing said CD34+ cells to a Notch ligand, in the presence of a fibronectin fragment containing an RGDS motif (SEQ ID No. 3, Arginine-Glycin-Aspartate-Serine), and/or a CS-1 motif and optionally a heparin-binding domain. Preferably, said fibronectin fragment contains an RGDS motif, a CS-1 motif and a heparin-binding domain.

This joint exposure of the CD34+ cells to the Notch ligand and to this fibronectin fragment also makes it possible to induce the differentiation of transduced CD34+ cells toward the T lymphoid pathway, thereby allowing the use of the process for grafts in gene therapy.

It is thought that the effect observed is due to the presence of the RGDS motif and/or of the CS-1 motif in the fibronectin fragment. Thus, the processes and methods described below are also applicable when using an RGDS peptide and/or a CS-1 peptide in place of the fibronectin fragment.

A joint use of the RGDS and CS-1 peptides is however preferred, in particular within the same protein.

If an RGDS peptide and/or a CS-1 peptide are used, they can thus be present as such in the culture medium, or present within a peptide or a protein present in said medium. When the culture medium contains only the RGDS peptide and/or the CS-1 motif as such, the expression peptide "free" in said medium will be used if this peptide is not immobilized on the lower wall of the container. Indeed, the peptide may be present in solution, or immobilized on the lower wall of the container in which the exposure of the CD34+ cells to the Notch ligand is carried out.

In the preferred embodiment, the invention relates to a method (or a process) for generating T-cell progenitors, comprising the step of exposing CD34+ cells in a medium containing a Notch ligand, in the presence of a fibronectin fragment. The Notch ligand is immobilized on a support. The fibronectin fragment contains an RGDS motif, a CS-1 motif and a heparin-binding domain.

The process according to the invention is carried out in vitro, in a container (such as a cell culture dish (Petri dish, 24-well plate, etc.)) on the lower wall of which the Notch ligand is immobilized. The Notch ligand can also be immobilized on any other support present in the reaction medium, in particular at the surface of microbeads. The aim of the immobilization of the Notch ligand is essentially to stabilize the ligand so as to allow the activation of the Notch receptor.

The term "T-cell progenitor" is intended to denote any cell committed into the pathway for differentiation toward the T lymphoid pathway from a CD34+HSPC. This cell is thus characterized in that it expresses the CD7 marker, which is known to be one of the markers which appears the earliest during T cell lymphoiesis. Depending on the state of differentiation in the T lymphoid pathway, it may or may not express the CD34 marker (loss of CD34 during differentiation).

Among "T-cell progenitors" mention is made of cells which can be found in the post-natal thymus, that is to say early thymic progenitor (ETP) cells proT1 cells (CD34+/CD45RA+/CD7+), (CD34+CD45RA+CD7++CD5-CD1a−), proT2 cells (CD34+CD45RA+CD7++CD5+CD1a−), and preT cells (CD34-CD7++/CD5+CD1a+). These cells are well known in the prior art. They are in particular mentioned by Reimann et al. (2012, op. cit.) and by Awong et al. (2009, op. cit.).

The term "RGDS peptide" is intended to denote any peptide or any protein containing the RGDS motif, such that it can bind to the VLA-5 integrin (see hereinafter). Such a peptide or such a protein can be tested via its capacity to eliminate the interaction of fibronectin with this VLA-5 integrin, by methods widely documented in the art.

The RGDS peptide binds to the VLA-5 (Very Late Antigen-5) integrin, which is a dimer composed of CD49e (alpha5) and of CD29 (beta1).

The heparin-binding domains are known in the art and are present in many heparin-binding proteins. They are generally in the form XBBXBX and XBBBXXBX (B=basic amino acid; X=hydropathic amino acid; Cardin and Weintraub, Arterioscler Thromb Vasc Biol. 1989; 9:21-32, SEQ ID No. 4 and SEQ ID No. 5).

The presence of such a heparin-binding domain is particularly advantageous when the CD34+ cells are also exposed to a retroviral vector for the purpose of transducing them, in order to obtain T-cell progenitors expressing a transgene.

A CS-1 peptide or CS-1 motif is a peptide of 25 amino acids (DELPQLVTLPHPNLHGPEILDVPST, SEQ ID No. 6), which was described by Wayner et al., 1989, J. Cell Biol. 109: 1321. This CS-1 motif binds to the VLA-4 (Very Late Antigen-4) receptor. This antigen is a dimeric integrin composed of CD49d (alpha 4) and of CD29 (beta 1).

In one particular embodiment, the fibronectin fragment is present in the culture medium or immobilized on the lower wall of the container. Fibronectin is a protein which, in its natural form, is a large v-shaped dimer 100 nm in length and of 460 kDa. The two monomers are linked by two disulfide bridges at their C-terminal end. The term "fibronectin" is intended to denote the natural fibronectin protein (that is to say any isoform produced by alternative splicing), but also a monomer of this protein, or a fragment of this protein (but containing the RGDS peptide, and also CS-1 peptide and the heparin-binding site).

A fibronectin that is particularly suitable for carrying out the process according to the invention is the protein RETRONECTIN®, which to corresponds a fragment of a human fibronectin (fragment CH-296; Kimizuka et al., J Biochem. 1991 August; 110(2):284-91; Chono et al., J Biochem. 2001 September; 130(3): 331-4) and contains the three functional domains that are preferred in the context of the implementation of the process (the C domain for binding to cells containing the RGDS peptide, the heparin-binding domain and the CS-1 sequence). This protein is already used to improve transduction using retroviral vectors (Chono et al., op. cit.), by allowing colocalization of the target cells (binding to integrins VLA-4 and VLA-5) and of the virions (which bind to the heparin-binding domain). This protein is in particular sold by the company Takara Bio Inc. (Shiga, Japan).

It is surprising and unexpected that this protein can also improve the differentiation of CD34+ cells into T-cell progenitors, including when it is desired to obtain such progenitors for cells transduced with a viral vector, in the context of a gene therapy, and also for adult cells.

As discussed above, but without wanting to be bound by this theory, this improvement in the CD34+ cell differentiation is probably linked to the presence of the RGDS motif which binds to the VLA-5 integrin, present on the cells, and/or of the CS-1 motif which binds to the VLA-4 receptor.

In one particular embodiment, the fibronectin fragment is immobilized (that is to say is bound to a solid support) and is not present free in solution (even though it is possible for some elements to possibly be found therein if they detach from the support). This solid support is preferentially the lower wall of the container in which the process is carried out. However, it is also possible to envision bonding the fibronectin fragment to beads, such as polymer beads or magnetic beads (having a diameter generally between 1 μm and 5 μm). The bonding of the protein or of the peptide to these beads may be covalent or noncovalent. The methods for attaching a protein or a peptide to a bead are well known in the art. This fibronectin fragment can also be introduced into a semi-solid medium, such as an agar or a gel.

When the fibronectin fragment is immobilized on the support (in particular the lower wall of the container in which the process is carried out), this immobilization may also be covalent or noncovalent. In one preferred embodiment, this immobilization is carried out noncovalently by allowing the fibronectin fragment to be absorbed onto the glass or plastic of which the lower wall of the container is made.

In one particular embodiment, as seen above, both the differentiation of CD34+ the cells into T-cell progenitors and the transduction of said CD34+ cells using a viral vector in order to introduce a gene of interest into these cells are carried out. This means that the cells exposed to the Notch ligand and to the fibronectin fragment are also exposed to a viral supernatant, during at least a part of the time during which they are exposed to the Notch ligand and the fibronectin fragment.

In fact, the inventors have been able to demonstrate that, when pretransduced cells are exposed to the Notch ligand (in particular DL-4), the production of T lymphocytes in vivo slower when is than the transduction is carried out at the same time as the exposure to DL-4. The joint exposure thus makes it possible to accelerate the production of T cells in vivo (after transplantation).

A second advantage of this joint exposure of the cells to the viral supernatant and to the Notch ligand (in particular DL-4) is to shorten the culture period (7 days instead of 11 days).

It should be noted that a joint exposure of the cells to the viral supernatant and to the Notch ligand (in particular DL-4) without the presence of the fibronectin fragment also makes it possible to accelerate the production of T-cell progenitors, and is another aspect of the invention, according to the same modes as in the presence of the fibronectin fragment.

Thus, in one preferred embodiment, the process is begun by exposing the cell to the Notch ligand and fibronectin fragment for a certain period of time (preferably greater than 4 hours, and more preferably greater than 6 h, or even greater than 8 h or greater than 10 h, but preferentially less than 36 hours, more preferably less than 30 h, more preferably less than 24 h), in the presence of cytokines, thereby allowing the cells to enter the division (preactivation) cycle, and then the viral supernatant is added for a certain period of time (preferably greater than 4 hours, more preferably greater than 6 h, or even greater than 8 h or greater than 10 h, but preferentially less than 30 hours, more preferably less than 24 h, more preferably less than 16 h on average).

If it is observed that the number of transduced cells is insufficient, it is possible to perform a second transduction, by again exposing the cells to the viral vector according to the modes described above.

This embodiment is in particular implemented when it is desired to perform an autologous transplantation of hematopoeitic stem cells in the context of a gene therapy protocol. Thus, the transgene introduced by a transduction with the viral supernatant is intended to express a protein that is absent or deficient in the patient in order to provide said patient with a therapeutic benefit. Among the transgenes that can be used (without this list being limiting or exhaustive), mention may be made of genes which allow therapy for immunodeficiencies (in particular severe combined immunodeficiencies, SCID or non-SCID, CID), HIV, X-linked adrenoleukodystrophy, hemoglobinopathies, in particular β-thalassemia or sickle-cell anemia. Innate or acquired immunodeficiencies such as AIDS, due to HIV, are thus diseases that can be targeted by gene therapy strategies.

The transduction is preferentially carried out with a retroviral supernatant which allows insertion of the transgene into the genome of the cell. The vectors, in particular lentiviral vectors, present in said supernatant are particularly suitable for this type of application and have been widely described in the literature.

Thus, the medium may also contain a viral vector intended for the transduction of said CD34+ cells, in the implementation of the process according to the invention. In one particular embodiment, this viral vector is introduced after a period of preactivation of the cells in the medium (culture in the presence of cytokines which allow the cells to enter the division cycle), of between 4 h and 36 h, preferably between 6 and 24 h. The viral vector is maintained in the medium in contact with the cells for a period of between 4 h and 30 h, preferably between 12 h and 24 h, more preferably for approximately 16 h, and is then removed from the medium. To "remove" the viral vector from the medium, the cells are harvested, washed and put back in culture in the preence of the Notch ligand and of the fibronectin fragment.

In one particular embodiment, said Notch ligand is the Delta-like-1 protein (SEQ ID No. 1) or fragment (soluble domain).

In another embodiment, the Notch ligand is the Delta-like-4 protein (SEQ ID No. 2).

In one particular embodiment, said Notch ligand is a fusion protein comprising the soluble domain of a natural Notch ligand, fused to an Fc region of an IgG domain of protein. The soluble a Notch ligand represents the extracellular part of said ligand. This is well known. Thus, Varnum-Finney et al. (J Cell Sci. 2000 December; 113 Pt 23:4313-8) have described a fusion protein made from fusion of the soluble part of DL-1 with an Fc portion of an IgG1. Reimann et al. (op. cit.) have described a fusion protein made from fusion of the soluble part of DL-4 (amino acids 1-526) with the Fc fragment of an IgG2b immunoglobulin. It is thus preferred when the IgG protein is an IgG2.

The culture medium used in the context of the present invention is any medium suitable for culturing CD34+ cells and T cells. Mention may in particular be made of the α-MEM, DMEM, RPMI 1640, IMDM, BME, McCoy's 5A and StemSpan™ (Stem Technologies) media or Fischer medium. A culture medium which is perfectly suitable and preferred for carrying out the process according to the invention is the X-VIVO™ 20 medium (Lonza, Basle, Switzerland). This medium has been used in particular by Jonuleit et al. (Eur J Immunol, 1997, 27, 12, 3135-42) and Left et al. (J Immunol, 1998, 161, 4, 1947-53).

Preferably, a basal medium (that is to say a medium which allows the cells to grow without it being necessary to add supplements thereto) is used, which will however be supplemented with serum, and also growth factors and cytokines.

Thus, fetal bovine serum (FBS) or fetal calf serum (FCS), autologous human serum or human AB serum is preferentially added to the basal culture medium. Preferably, this medium is supplemented with at least 15% of fetal serum, more preferably at least 20%. FBS is particularly suitable for carrying out this process. In particular, defined FBS is preferably used. Defined FBS is a high-quality serum which has been analyzed and filtered to prevent the presence of viral particles. It is sold as such by numerous suppliers, such as HyClone™ Defined Fetal Bovine Serum from (FBS) Thermo Scientific™.

The culture medium is also preferentially supplemented with cytokines and growth factors. These cytokines and growth factors are in particular chosen from the group consisting of SCF (stem cell factor), thrombopoietin (TPO, also called megakaryocyte growth and development factor, MGDF), Flt3-ligand (which is a hematopoietic growth factor), interleukin 3 (IL-3), interleukin 7 (IL-7) and SCF (stem cell factor). In one particular embodiment, the culture medium contains at least three, preferentially at least four, of these cytokines or growth factors.

In one preferred embodiment, and in particular for generating T lymphocyte precursors not transduced with a viral vector, at least or exactly three cytokines are added.

Preferably, these three cytokines are interleukin-7 (IL-7), SCF (stem cell factor) and Flt-3 ligand (hematopoietic growth factor).

In another preferred embodiment, four cytokines, that is to say the three cytokines mentioned above and TPO (thrombopoietin), are added.

In another particular embodiment, and in particular for generating T lymphocyte precursors transduced with a viral vector, the nature of the cytokines and growth factors can be varied during the implementation of the process.

Thus, it is possible to use IL-3, IL-7, SCF, TPO and Flt3-L in the medium, if the cell preactivation step is carried out before adding the viral vector, and then to supplement the medium only with IL-7, SCF, TPO and Flt3-L after the vector has been removed.

The mixtures of cytokines and growth factors mentioned above are sufficient to induce the differentiation of the CD34+ cells into T lymphocyte precursors and, generally, the culture medium comprises no other cytokine or growth factor.

In the context of the process, the total exposure time of the CD34+ cells in the presence of the Notch ligand and of the protein or peptide having the RGDS motif is generally a period preferentially greater than 3 days, and less than 10 days.

This exposure can vary according to whether or not the cells are transduced. Thus, an exposure time of three days can prove to be sufficient for non-transduced adult stem cells, whereas it will generally be longer in the case of transduction or of infantile stem cells (approximately 7 days).

The CD34+ cells are obtained from a blood sample from a donor, from a bone marrow puncture or from umbilical cord blood. The methods for sorting the CD34+ cells are known in the art. Magnetic beads which have an antibody that recognizes CD34+ at their in surface can particular be used to do this.

Preferably, the cell culture container is prepared by immobilizing the Notch ligand and the fibronectin fragment on the lower surface, before exposing the CD34+ cells.

RETRONECTIN® or another fibronectin naturally adheres to the plastic of the cell culture dish (Petri dish or 24-well plate, or the like).

Likewise, if a Notch ligand is used as fusion protein made from fusion with the Fc fragment of an immunoglobulin, this Fc fragment also adheres to the plastic.

It is thus sufficient to leave the container in the presence of these compounds for a few hours in order to obtain the appropriate coating.

In particular, the following protcol can be used to cover the lower surface with the Notch ligand fused with an Fc fragment, and RETRONECTIN®:
  prepare a solution containing the Notch ligand (5 µg/ml) and RETRONECTIN® (25 to 50 µg/ml) in PBS (phosphate-buffered saline). However, it is also possible to use amounts of RETRONECTIN® that are as low as 10 to 15 µg/ml without reducing the results;
  cover the wells of a cell culture dish with this solution: 0.5 ml for a 24-well plate; 1.0 ml for a 6-well plate;
  leave the proteins to deposit for 24 h at 4° C. (or even 48 to 72 hours), or for approximately 2 h at 37° C.;
  wash with PBS (at the working temperature);
  use a blocking agent (PBS+2% BSA (bovine or human serum albumin) or HA (human hemagglutinin) agent (0.5 ml for the 24-well plates; 2 ml for the 6-well plates) for 1 h at 37° ° C.;
  wash with PBS at 37° C.

It is clear that the setting up of other concentrations or other conditions for coating is routine work for those skilled in the art, if they use other proteins or other cell culture containers (flasks, bags, etc.).

In particular, the inventors have shown that, at the concentration of 5 µg/ml, approximately 75% of the DL-4 binds to the surface of the container. Various doses of DL-4 have been tested and it is preferable for the concentration to be greater than equal or to 1.25 µg/ml, an optimal concentration being between 2.5 and 5 µg/ml.

With regard to the RETRONECTIN®, the concentration of 25 µg/ml is perfectly suitable, although other concentrations (higher or lower) can also be suitable.

The invention thus also relates to a cell culture container, characterized in that at least one of the surfaces thereof is covered with a Notch ligand and with a protein or a peptide having the RGDS and/or CS-1 motif, and in particular a fibronectin fragment as described above.

Preferably, the Notch ligand is the soluble part of the natural Notch ligand (in particular DL-1 or DL-4) and is fused with an Fc fragment of an immunoglobulin (such as an IgG1 or an IgG2).

Preferably, it is DL-4. Preferably, the Fc fragment is derived from an IgG2. In one preferred embodiment, the Notch ligand immobilized at the surface of the culture dish (and used in the context of the process according to the invention) has the sequence SEQ ID No. 7.

Preferably, in this embodiment, the protein which has the RGDS motif is as described above. It is preferentially a fibronectin and in particular RETRONECTIN®.

Thus, preferably, the cell culture dish has at least one surface which has been covered with a DL-4/IgG2 Fc fragment fusion protein and with RETRONECTIN®.

The concentrations are as mentioned above, and the container has been obtained in particular by the method described above, that is to say a step of adding a solution containing the Notch ligand, the protein or the peptide having the RGDS and/or CS-1 motif, in particular the fibronectin fragment, to said container, a step of leaving to stand allowing the proteins to deposit and to adhere to the walls of the container, followed by steps of rinsing and preferentially blocking the walls of the container with a non-reactive protein (such as a serum albumin).

In the implementation of the process according to the invention, the cells are added at a concentration of between $10^6$ and $10^7$ CD34+ cells/ml, in particular of about $2 \times 10^6$ CD34+ cells/ml to the culture container. Depending on the amount of CD34+ to be transduced, a dish ranging from 2 to 10 cm² (or respectively a plate ranging from 24 wells to 6 wells) may be used. Preferably, when a 24-well plate is used, each well is inoculated with between $10^5$ and $10^6$ CD34+ cells per well, preferentially about $2 \times 10^5$ to $4 \times 10^5$ CD34+ cells per well. In the case of a 6-well culture plate, between $8 \times 10^5$ and $2 \times 10^6$ cells per well are instead used.

The amount of cells to be inoculated can be easily adjusted by those skilled in the art depending on the container that they use.

The cells are placed in the well in the basal medium chosen, preferentially supplemented with cytokines or growth factors, as seen above.

The concentrations of these cytokines or growth factors are between 2 and 300 ng/ml.

Preferably, the cytokines are added at a concentration generally greater than 40 ng/l and less than 300 ng/ml or 200 ng/l, more preferably at a concentration of about 100 ng/ml.

However, when it is desired to generate transduced T-cell progenitors and the cells are preactivated before placing them in the presence of the viral vector, it is possible to use higher concentrations (of about 300-400 ng/ml). In this embodiment, SCF and Flt3-L can be used at concentrations of about 300 ng/ml, TPO and IL-7 at concentrations of about 100 ng/ml, and IL-3 at approximately 40 ng/ml.

In one preferred embodiment, the exposure time of the cells to the Notch ligand and to the fibronectin fragment is preferentially greater than or equal to 3, or even greater than or equal to 5, days. It is generally less than 10 days, or even less than 8 days. An advantageous time is preferably between 5 and 8 days, that is to say approximately 7 days. If it is desired to exceed 7 days of culture, it is preferable to transfer the cells into new containers coated with the Notch ligand and with the fibronectin fragment. This time depends in particular on the origin of the CD34+ cells. Thus, the exposure time can be shorter for CD34+ cells obtained from an adult than for cells obtained from a child or from cord blood. This is particularly surprising, in the light of the prior art and of the a priori lesser capacity for differentiation of adult stem cells. The transduced cells are generally exposed for a longer time than the non-transduced cells.

After having generated the T-cell progenitors, by means of the process described above, it is possible to purify these T-cell progenitors thus generated. This purification is carried out by washing the cells and suspending in a suitable basal medium.

These T-cell progenitors can also be packaged in a bag in order to be able to inject them into a patient. In this case, these cells are repackaged in a saline solution containing HSA at 5%, such as 5% albunorm™ 50 g/l (Octopharma, Lingolsheim, France).

These cells can also be frozen according to the methods known in the art.

The invention also relates to T-cell progenitors for their use in an immunodepressed patient, in particular for enabling immune reconstitution in this patient and/or obtaining immune protection against infections in said patient for a period of about a few months (approximately at least two months, preferably approximately at least six months). In one particular embodiment, the patient is an immunodepressed patient. There may be many reasons for the deficiency: hereditary immune deficiency, chemotherapy for leukemia, conditioning, graft containing only stem cells, post-graft prophylatic treatment for GVH (graft-disease), age of the versus-host recipient, and complications of infection type. The patient may thus in particular be immunodepressed because of the depletion of his or her immune cells following therapy before a bone marrow graft. In this embodiment, the graft may be an allograft (in this case, the T-cell from a donor who is progenitors are preferentially partially HLA-compatible with patient), or an autograft (in which case the T-cell progenitors have preferentially been transformed with a vector in order to express a gene and/or a protein making it possible to correct a genetic defect in said patient).

In one particular embodiment, the T-cell progenitors have been obtained by exposing CD34+ cells in the presence of a Notch ligand (as described above) and of a protein or peptide having the RGDS motif and/or the CS1 motif, in particular a fibronectin fragment as described above, under the conditions mentioned above. In this embodiment, it is thus preferable for the exposure to be less than or equal to 10 days.

The T-cell progenitors envisioned exhibit in particular the CD7 marker, and may or may not express the CD34 marker.

The invention relates to a method for treating an immunodepressed patient, in particular with a view to enabling at least temporary immune reconstitution in this patient, comprising the step of adminstering to said patient T-cell progenitors, as described above. This method can also include the step of obtaining such progenitors by exposing CD34+ cells to a Notch ligand (as described above) and a protein or peptide having the RGDS motif and/or the CS1 motif, in particular a fibronectin fragment as described above, under the conditions mentioned above. A therapeutically effective amount, that is to say about 1 to $5 \times 10^6$/kg, of progenitors is in particular administered, thereby making it possible to provide the patient with cells capable of playing a protective role against infections for a few months (about 6 months).

Preferably, this administration of T-cell progenitors is carried out just before, just after or concomitently with a hematopoietic stem cell transplant in said patient. As seen above, the cells injected can be transformed with a vector enabling the correction of a genetic defect in said patient.

EXAMPLES

Example 1—Materials and Methods a) Preparation of the CD34+ Cells

The CD34+ cells are isolated by separation of the mononuclear cells on a Ficoll gradient and immunomagnetic sorting, as described in the prior art (Six et al., J Exp Med 2007 204: 3085).

b) Preparation of the Soluble Notch Ligand

The soluble Notch ligand is a fusion protein generated by cloning the soluble part of the Notch ligand and the constant part of human immunoglobulin, as described in Reimann et al. (2012, op. cit.). The sequence of the fusion protein is SEQ ID No. 7.

c) Preparation of the Containers
  i. Without RETRONECTIN®
    The container is composed of a culture well containing culture medium, on which the soluble Notch ligand has been immobilized according to the technique described in Reimann et al. (2012, op. cit.).
  ii. With RETRONECTIN®
    The RETRONECTIN® is immobilized at the same time as the soluble Notch ligand in the culture well. The RETRONECTIN® concentration is from 25 to 50 µg/ml. The work is carried out at ambient temperature or at 4° C., in a microbiological safety cabinet (MSC).

d) Exposure of the CD34+ Cells

The CD34+ cells are placed in culture in the container at a concentration of between $2 \times 10^4$ and $1.5 \times 10^5$ cells/ml. The culture lasts for between 3 and 10 days, as described in Reimann et al. (2012, op. cit.).

e) Analysis of the CD34+ Cells

The analysis of the cultured cells comprises: counting the living cells, analysis, by flow cytometry, of the expression of the CD34, CD7 and optionally CD5 and CD1a markers and by secondary co-culture under limiting dilution conditions on an OP9/DL-1 stroma which makes it possible to quantify the T precursors generated by the culture (Reimann C Stem Cells 2012, 30(8): 1771-80). It is optionally completed by an analysis of the gene expression profile by quantitative RT-PCR relating to molecules that are important for the commitment and differentiation of the CD34+ cells to T lymphocytes (TCF7, GATA3, RAG1, IL7R, BCL11B, LEF1, PTCRA).

Example 2—Comparison of the Results Obtained in the Presence or Absence of RETRONECTIN®, in the Absence of Transduction of the Cells 1. Results Obtained with Cord Blood CD34+ Cells (6 Experiments)

Figure 1:
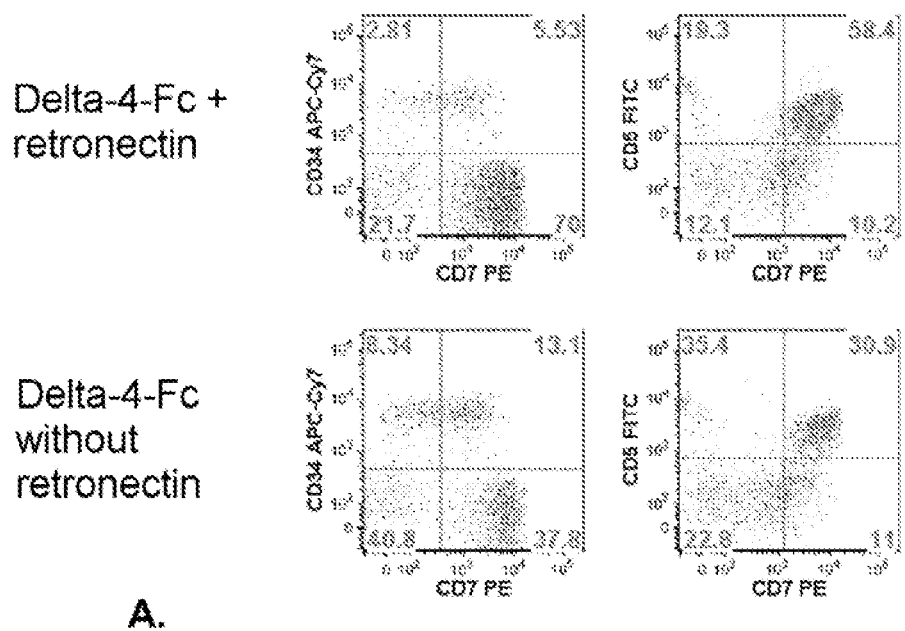
FIG. 1: comparison of the number and percentage of percentage and of the number of CD7+CD34+/− cells obtained after culturing CD34+ cells in the absence (−RN) or presence (+RN) of RETRONECTIN® (RN). A. Flow cytometry analysis of the expression of the CD34, CD7 markers. B. Representation of the number of CD34-CD7+ cells (for six independent experiments).
Figure 1:
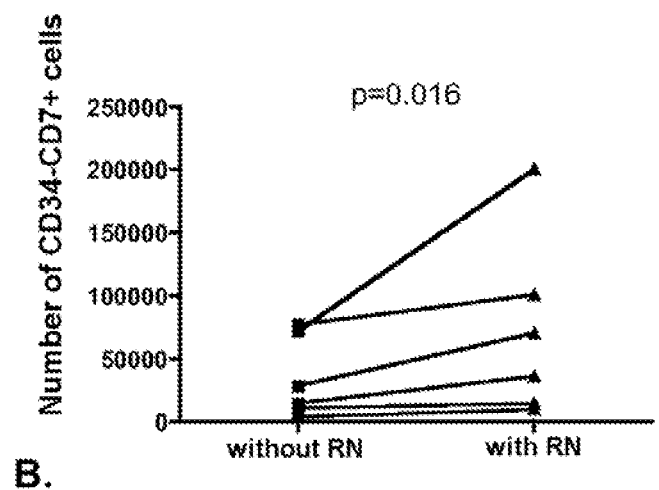

An increase in the percentage and number of CD7+CD34+/− cells obtained after culture in the presence of RETRONECTIN® is observed (FIG. 1).

An increase in the frequency of T precursors present in the culture at D7 and measured under limiting dilution conditions by coculture on OP9/DL-1 is also observed (table I).

TABLE I

| T precursors at D7 ($2 \times 10^4$ CD34+ at D0) | Frequency | Number |
|---|---|---|
| In the absence of RETRONECTIN ® | 1/30 | 733 |
| In the presence of RETRONECTIN ® | 1/21 | 2108 |

Figure 2:
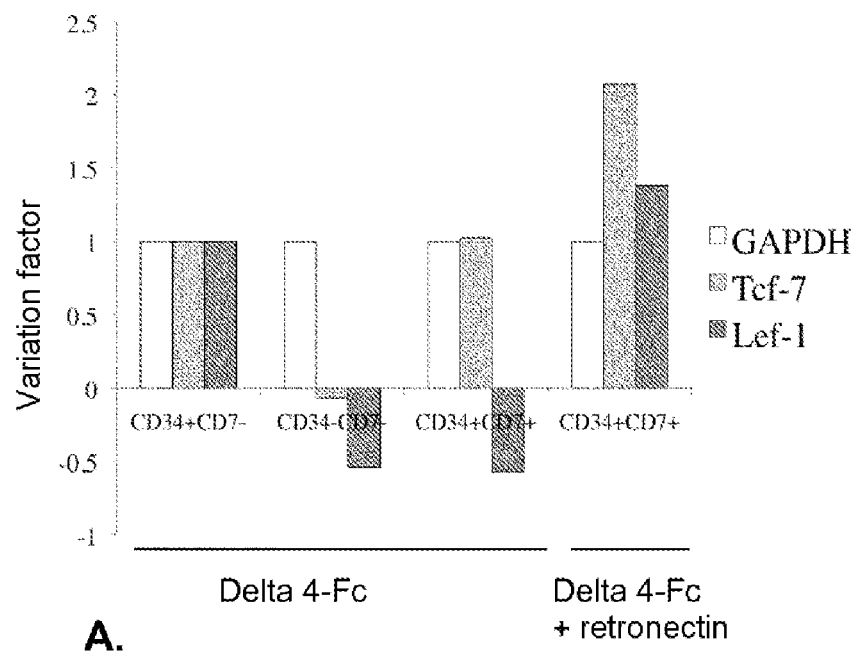
FIG. 2: comparison of the expression (relative to the GAPDH (glyceraldehyde-3-phosphate dehydrogenase) control) of genes involved in the differentiation of CD34+ cells into T lymphocytes. A. Tcf-7 (transcription factor 7) and Lef-1 (lymphoid enhancer-binding factor 1) genes. G. Bcl11b (B-cell CLL/lymphoma 11B) and LCK (lymphocyte-specific protein tyrosine kinase) genes.
Figure 2:
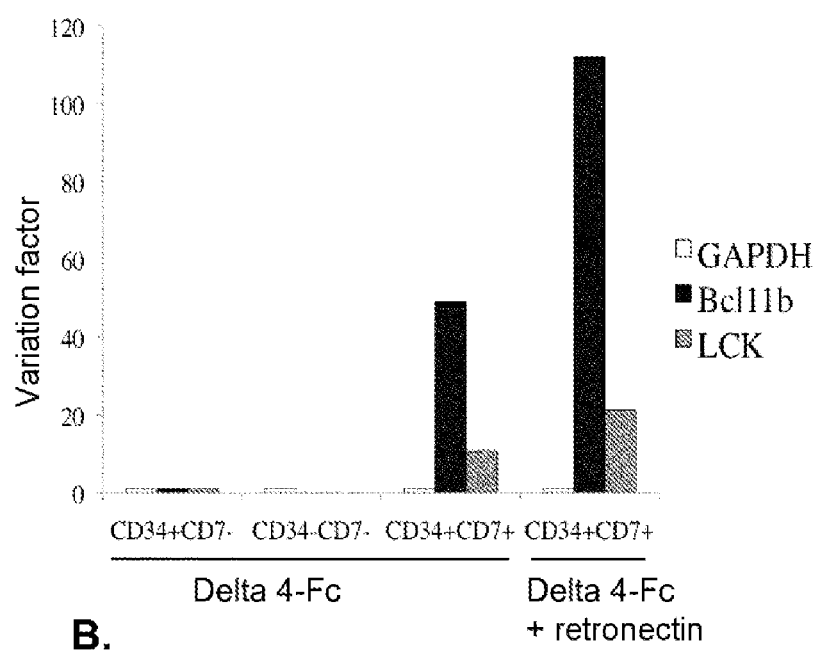

An increase in the expression (relative to the GAPDH (glyceraldehyde-3-phosphate dehydrogenase) endogenous gene) of genes involved in the differentiation of the CD34+ cells into T lymphocytes can also be observed (FIG. 2).

2. Results Obtained with Mobilized Donor Blood CD34+ Cells

Figure 3:
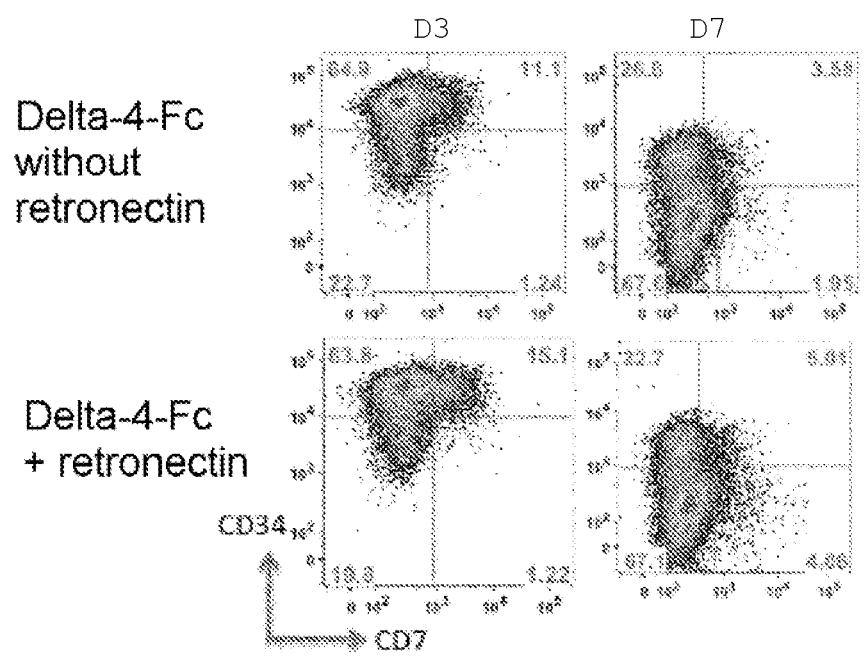
FIG. 3: comparison of the percentage of CD7+CD34+/− cells obtained after culturing in the presence or absence of RETRONECTIN® (flow cytometry analysis of the expression of the CD34, CD7 markers), obtained by culturing of mobilized donor blood CD34+ cells.

An increase in the percentage of CD7+CD34+/− cells after culture in the presence of RETRONECTIN®, relative to what is obtained after culture in the absence of RETRONECTIN®, is observed (FIG. 3).

An increase in the frequency of T precursors present in the culture at D7 and measured under limiting dilution conditions by coculture on OP9/DL-1 is also observed (tables II and III).

Results obtained from $10^5$ CD34+

TABLE II

| | Absence of RETRONECTIN ® | | Presence of RETRONECTIN ® | |
|---|---|---|---|---|
| Exp 1 | Frequency | Total progenitors | Frequency | Total progenitors |
| D3 | 1/42 | 2133 | 1/33 | 3240 |
| D7 | 1/100 | 1600 | 1/46 | 2613 |

TABLE III

| | Absence of RETRONECTIN ® | | Presence of RETRONECTIN ® | |
|---|---|---|---|---|
| Exp 2 | Frequency | Total progenitors | Frequency | Total progenitors |
| D3 | 1/19 | 4109 | 1/10 | 8836 |
| D7 | 1/72 | 1654 | 1/19 | 6709 |

3. Conclusion

These results clearly show that the joint presence of RETRONECTIN® and the DL-4 ligand makes it possible to improve the generation of precursors involved in the T lymphoid differentiation pathway (T-cell progenitors) from CD34+ stem cells.

Example 3—Results Obtained in the Presence of RETRONECTIN®, for Transduced Cells The CD34+ cells of a patient's bone marrow are preactivated for 24 h at the concentration of $2 \times 10^6$ cells/in an X-vivo20 medium containing 300 ng/ml SCF, 300 ng/ml Flt3-L, TPO, 100 ng/ml 40 ng/ml IL-3, 100 ng/ml IL-7 and 20% serum on a substrate obtained after having covered the culture plates with a solution of RETRONECTIN® at 50 µg/ml and DL4/Fc at 5 µg/ml.

Between D1 and D2, the cells are subjected to transduction using the viral vector in the preactivation medium enriched with protamine sulfate at 4 µg/ml.

On D3, the cells are harvested, washed and placed back in culture until D7 on a DL4/Fc protein substrate in a medium supplemented with serum (20%), SCF (100 ng/ml), Flt-3L (100 ng/ml), TPO (100 ng/ml) and IL-7 (100 ng/ml).

This allows the CD34+ progenitors to enter the T differentiation pathway, this being attested to by the appearance of a large number of cells bearing the CD7 marker.

The proof of this commitment is confirmed by the considerably accelerated production of T lymphocytes.

The in vitro experiments revealed that, at the end of the transduction of the CD34+ HSCs, the culture in the presence of DL4/Fc and of the RETRONECTIN® fragment contains CD34+/−CD7+T lymphoid progenitors (14%). The appearance of double-positive CD4+CD8+T lymphocytes (8%) and of CD3+T lymphocytes (8%) is also observed from D25, whereas the conventional protocol of transduction alone (without exposure to DL4/Fc+ RETRONECTIN®) only makes it possible to obtain less than 1% of (CD4+CD8+ or CD3+) T lymphocytes at D25.

In vivo, the transplantation of the progenitors generated according to the protocol defined, into NOD/SCID/γc ko mice, shows the induction of human thymopoiesis approximately 6 weeks after the transplantation of cells transduced and exposed to DL-4/Fc+ RETRONECTIN®

No thymopoiesis is observed in the recipients of cells transduced under the conventional conditions.

The invention claimed is:

1. An in vitro method of differentiating human cells that express CD34 into T-cell progenitors that express CD7 and optionally CD34, the method comprising culturing human cells that express CD34 for a period of between 3 to 8 days in the presence of:
   (i) a medium,
   (ii) a Notch ligand immobilized on a support, wherein the Notch ligand comprises a soluble domain of a Delta-like-4 ligand, fused to an Fc region of an IgG protein, and
   (iii) a fibronectin fragment comprising an RGDS motif and/or a CS-1 motif,
   such that T-cell progenitors that express CD7 and optionally CD34 are obtained.

2. The method process of claim 1, wherein said IgG protein is an IgG2 protein.

3. The method process of claim 1, wherein said fibronectin fragment is fragment CH-296 of human fibronectin.

4. The method of claim 1, wherein said fibronectin fragment is immobilized on said support or on at least one other support.

5. The method of claim 1, wherein said medium comprises a viral vector for at least a portion of the culturing period.

6. The method of claim 5, wherein the viral vector is a lentiviral vector.

7. The method of claim 5, wherein the viral vector is introduced in the medium after a period of preactivation of the CD34+ cells of between 4 hours and 36 hours.

8. The method of claim 5, wherein the T cell progenitors expressing CD7 and optionally CD34 are for use in a method for treating a patient, and wherein the viral vector encodes a protein that is absent or deficient in the patient.

9. The method of claim 1, wherein the medium comprises at least 15% of FBS.

10. The method of claim 1, wherein the medium comprises at least three cytokines selected from the group consisting of interleukin 7 (IL-7), stem cell factor (SCF), thrombopoietin (TPO) and the Flt3 ligand (FLT3L).

11. The method of claim 10, wherein the medium comprises IL-7, SCF, TPO and FLT3L.

12. The method of claim 1, further comprising purifying the T-cell progenitors.

13. The method of claim 12, further comprising packaging said T-cell progenitors in a bag.

14. The method of claim 1, wherein the fibronectin fragment comprises a heparin-binding domain.

15. The method of claim 1, wherein the fibronectin fragment comprises an RGDS motif, a CS-1 motif, and a heparin-binding domain.

16. The method of claim 1, wherein said fibronectin fragment is immobilized on beads.

* * * * *